United States Patent
Collins

(10) Patent No.: US 10,478,221 B2
(45) Date of Patent: Nov. 19, 2019

(54) INTRODUCER FOR INTRODUCTION OF A PROSTHESIS INTO A LUMEN OF A PATIENT

(71) Applicant: Cook Medical Technologies LLC, Bloomington, IN (US)

(72) Inventor: James Collins, Paddington (AU)

(73) Assignee: Cook Medical Technologies LLC, Bloomington, IN (US)

( * ) Notice: Subject to any disclaimer, the term of this patent is extended or adjusted under 35 U.S.C. 154(b) by 8 days.

(21) Appl. No.: 15/626,295

(22) Filed: Jun. 19, 2017

(65) Prior Publication Data

US 2018/0360491 A1 Dec. 20, 2018

(30) Foreign Application Priority Data

Jun. 19, 2017 (AU) ................................ 2017204135

(51) Int. Cl.
*A61B 17/34* (2006.01)
*A61M 25/00* (2006.01)
(Continued)

(52) U.S. Cl.
CPC ...... *A61B 17/3468* (2013.01); *A61B 17/3462* (2013.01); *A61M 25/0097* (2013.01);
(Continued)

(58) Field of Classification Search
CPC ............ A61B 17/3468; A61B 17/3462; A61B 2017/00862; A61B 2017/3464;
(Continued)

(56) References Cited

U.S. PATENT DOCUMENTS 5,104,389 A * 4/1992 Deem ............... A61M 39/0606
604/167.02
5,250,033 A 10/1993 Evans et al.
(Continued)

FOREIGN PATENT DOCUMENTS

CN 102137644 1/2010
CN 203500627 3/2014
(Continued)

OTHER PUBLICATIONS

AU Application No. 2017204135 Examination Report No. 1, Cook Medical Technologies LLC, dated Jun. 19, 2017.
(Continued)

*Primary Examiner* — Lauren P Farrar
(74) *Attorney, Agent, or Firm* — Richard J. Godlewski

(57) ABSTRACT

An introducer and a delivery assembly for introduction of a prosthesis into a bodily lumen is disclosed. The introducer comprises: a sheath; a housing mounted to a distal end of the sheath, the housing having a passage there-through adapted to receive a delivery assembly; a port for introducing flushing fluid, the port communicating with the passage; and a liquid absorbing seal for sealably receiving the delivery assembly, the liquid absorbing seal disposed within the housing distally of the port. The delivery assembly comprises: a guide wire catheter; a tip mounted to a proximal end of the guide wire catheter; a distal delivery member mounted around the guide wire catheter and located distal of the tip; and a prosthesis receiving portion between the tip and the distal delivery member. The delivery assembly is slidably mounted through the introducer. Absorption of fluid swells the liquid absorbing seal.

10 Claims, 5 Drawing Sheets

(51) Int. Cl.
*A61M 25/06* (2006.01)
*A61F 2/966* (2013.01)
*A61M 25/01* (2006.01)
*A61B 17/00* (2006.01)

(52) U.S. Cl.
CPC .............. *A61M 25/0662* (2013.01); *A61B 2017/00862* (2013.01); *A61B 2017/3437* (2013.01); *A61B 2017/3464* (2013.01); *A61F 2/966* (2013.01); *A61M 25/0102* (2013.01); *A61M 2025/0062* (2013.01); *A61M 2025/0681* (2013.01)

(58) Field of Classification Search
CPC ............ A61B 2017/3437; A61F 2/966; A61M 25/0097; A61M 25/0062; A61M 25/0102; A61M 2025/0062; A61M 2025/0681
See application file for complete search history.

(56) References Cited

U.S. PATENT DOCUMENTS

| | | | |
|---|---|---|---|
| 5,720,730 | A | 2/1998 | Blake, III |
| 7,412,290 | B2 | 8/2008 | Janke et al. |
| 7,651,519 | B2 | 1/2010 | Dittman |
| 9,078,981 | B2 | 7/2015 | Subramaniam et al. |
| 2004/0210194 | A1* | 10/2004 | Bonnette ................ A61B 17/22 604/167.06 |
| 2008/0243092 | A1* | 10/2008 | Nilsson ............. A61M 25/0606 604/272 |
| 2010/0069949 | A1 | 3/2010 | Chin et al. |
| 2014/0100605 | A1 | 4/2014 | Khosravi et al. |
| 2014/0276611 | A1 | 9/2014 | Banerjee |
| 2015/0105752 | A1 | 4/2015 | Gordon et al. |
| 2015/0150679 | A1* | 6/2015 | Jimenez ................ A61F 2/2418 623/2.11 |
| 2016/0310270 | A1 | 10/2016 | Nguyen et al. |

FOREIGN PATENT DOCUMENTS

| | | |
|---|---|---|
| EP | 2404577 A1 | 1/2012 |
| EP | 2450081 A2 | 5/2012 |
| EP | 2318087 B1 | 8/2016 |
| JP | 2015157144 | 8/2016 |
| JP | 20150157144 | 8/2016 |
| WO | 2010008571 A1 | 1/2010 |

OTHER PUBLICATIONS

AU Application No. 2017204135 Prior Art Disclosure Statement, Cook Medical Technologies LLC, dated Jun. 19, 2017.
Examination Report No. 1 for Application No. AU2017204135, Cook Medical Technologies LLC, dated Jun. 19, 2017.
Prior Art Disclosure Statement for Application No. AU2017204135, Cook Medical Technologies LLC, dated Jun. 19, 2017.
Extended EU Search Report, Application No. 18275074.5, Cook Medical Technologies LLC, dated Oct. 22, 2018.
Extended European Search Report, Application No. 18275074.5, Cook Medical Technologies LLC, dated Oct. 22, 2018.

* cited by examiner

US 10,478,221 B2

INTRODUCER FOR INTRODUCTION OF A PROSTHESIS INTO A LUMEN OF A PATIENT

CROSS REFERENCE TO RELATED APPLICATIONS

This application claims the benefit of Australian patent application No. 2017204135 filed on Jun. 19, 2017 entitled AN INTRODUCER FOR INTRODUCTION OF A PROSTHESIS INTO A LUMEN OF A PATIENT the entire contents of which are incorporated herein by reference.

FIELD

The present disclosure relates generally to the field of medical devices. Particular embodiments are related to medical devices that are deployable into bodily lumens including vascular systems.

BACKGROUND

A variety of medical devices have been developed for endovascular repair. For instance, various methods and devices have been developed to repair aneurysmal or occluded branches of the aorta. Many such devices include tubular introducers having internal passages, sometimes referred to as introducer catheters, that include a seal and/or valve to retard or stop blood flow through their internal passages. For instance, introducer catheters are known to employ Captor™ valves. Introducers are typically designed to track along a guide wire and some introducers are designed to seal against both small diameter guide wires and larger diameter portions of delivery devices.

Existing introducers and their seals/valves suffer a number of shortcomings. For instance, they leak blood more than is desirable. With some devices, this can be exacerbated or caused by storage before use. This is because seals are subject to "taking a set" or being deformed during prolonged storage. Where seals are deformed during storage, they may take a significant period of time to (or never) recover their optimum condition.

Another characteristic of many existing introducers and their seals or valves is the level of both static and dynamic sliding friction that resists relative movement between the introducers and delivery devices passing through them. In many applications it may be desirable to minimise or at least provide a low level of static and/or dynamic friction so as to assist a surgeon with fine manipulations of a delivery device passing through an introducer.

There is a need to minimise blood leakage through introducers, especially blood leakage around guide wires used in endovascular procedures. There is also a need to provide introducers that facilitate easy manipulation of delivery devices passing through them.

Throughout this specification, the term "distal" with respect to a portion of the aorta, a deployment device or an endograft means the end of the aorta, deployment device or endograft further away in the direction of blood flow from the heart and the term "proximal" means the portion of the aorta deployment device or end of the endograft nearer to the heart in the direction of blood flow. When applied to other vessels, similar terms such as caudal and cranial should be understood.

SUMMARY OF THE INVENTION

According to a first aspect of the invention there is provided an introduction of a prosthesis into a lumen of a patient, the introducer comprising:

a sheath having a proximal end and a distal end;

a housing mounted to the distal end of the sheath, the housing having a passage there-through adapted to receive a delivery assembly;

a port for introducing flushing fluid, the port communicating with the passage; and a liquid absorbing seal for sealably receiving the delivery assembly, the liquid absorbing seal disposed within the housing distally of the port, whereby introduction of a flushing fluid through the port into the passage results in absorption of a portion of the flushing fluid into the liquid absorbing seal.

In one form the liquid absorbing seal comprises hydrogel.

In one form the hydrogel comprises a lubricious polymer.

In one form the hydrogel is a hydrophilic thermoplastic polyurethane elastomer.

In one form the housing includes a cap, the cap retaining the liquid absorbing seal.

In one form the introducer further comprises a compression assembly, the compression assembly operable to compress the liquid absorbing seal.

In one form the compression assembly comprises an actuator and a compression segment.

In one form the actuator comprises a rotatable body, the rotatable body threadably connected to the housing, wherein the rotation of the rotatable body pushes the compression segment against the liquid absorbing seal thereby compressing the liquid absorbing seal.

In one form the compression segment is a separate component to the rotatable body and wherein the compression segment and the rotatable body are mutually arranged and constructed to allow relative rotation.

In one form the introducer further comprises a delivery assembly, the delivery assembly comprising:

a guide wire catheter;

a tip mounted to a proximal end of the guide wire catheter;

a distal delivery member mounted around the guide wire catheter and located distal of the tip; and a prosthesis receiving portion between the tip and the distal delivery, wherein the delivery assembly is slidably mounted through the introducer.

In one form in a first condition the liquid absorbing seal engages an external surface of the distal delivery member, wherein in a second condition the liquid absorbing seal engages an external surface of a guide wire, whereby in at least the second condition, absorption of fluid swells the liquid absorbing seal.

In one form the liquid absorbing seal comprises hydrogel.

In one form the hydrogel comprises a lubricious polymer.

In one form the hydrogel is a hydrophilic thermoplastic polyurethane elastomer.

In one form the housing includes a cap, the cap retaining the liquid absorbing seal.

In one form the introducer further comprises a compression assembly, the compression assembly operable to compress the liquid absorbing seal.

In one form the compression assembly comprises an actuator and a compression segment.

In one form the actuator comprises a rotatable body, the rotatable body threadably connected to the housing, wherein the rotation of the rotatable body pushes the compression segment against the liquid absorbing seal thereby compressing the liquid absorbing seal.

In one form the compression segment is a separate component to the rotatable body and wherein the compression segment and the rotatable body are mutually arranged and constructed to allow relative rotation.

In a second aspect of the invention there is provided an introducer and a delivery assembly for introduction of a prosthesis into a lumen of a patient, the introducer comprising:
- a sheath having a proximal end and a distal end;
- a housing mounted to the distal end of the sheath, the housing having a passage there-through adapted to receive a delivery assembly;
- a port for introducing flushing fluid, the port communicating with the passage; and
- a liquid absorbing seal for sealably receiving the delivery assembly, the liquid absorbing seal comprising a hydrophilic thermoplastic polyurethane elastomer, the liquid absorbing seal disposed within the housing distally of the port,
- and the delivery assembly comprising:
  - a guide wire catheter;
  - a tip mounted to a proximal end of the guide wire catheter;
  - a distal delivery member mounted around the guide wire catheter and located distal of the tip; and
  - a prosthesis receiving portion between the tip and the distal delivery member
  - wherein the delivery assembly is slidably mounted through the introducer, and
  - wherein in a first condition the liquid absorbing seal engages an external surface of the distal delivery member, and
  - wherein in a second condition the liquid absorbing seal engages an external surface of a guide wire,
  - whereby in at least the second condition, absorption of fluid swells the liquid absorbing seal.

DESCRIPTION OF PREFERRED EMBODIMENTS

Figure 1:
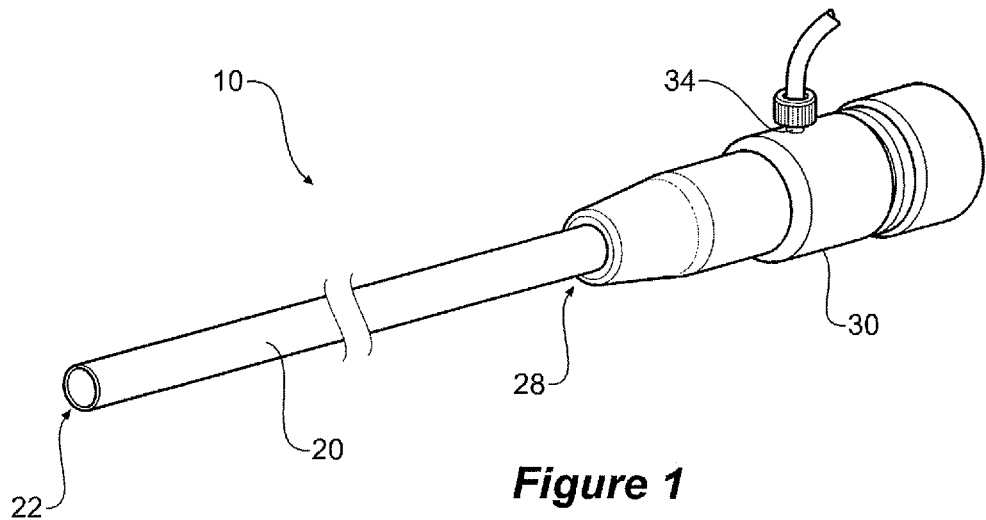
FIG. 1 is a diagrammatic isometric view of a generalised introducer according to the invention.
Figure 2:
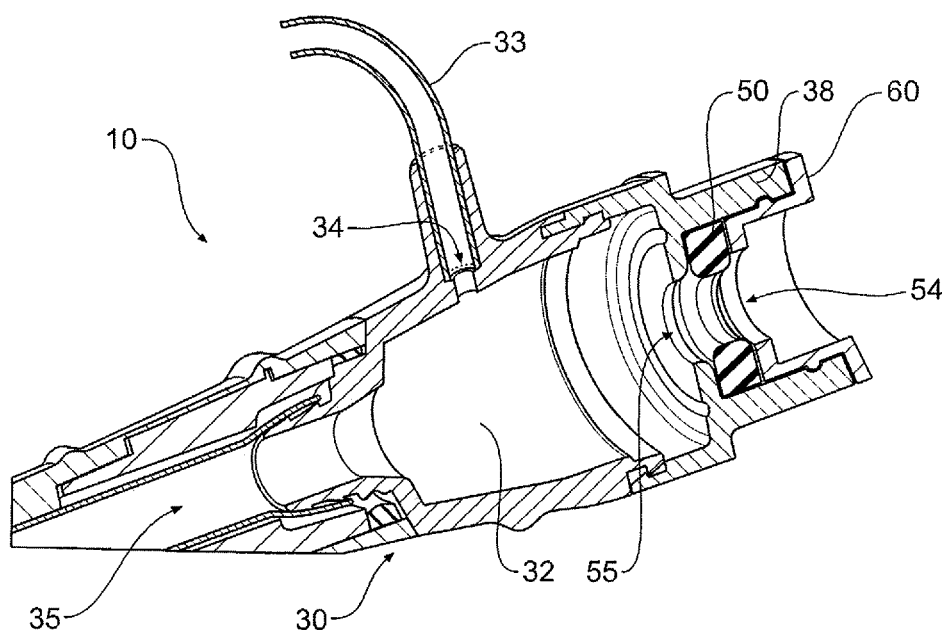
FIG. 2 is a close up cross-sectional view of a first embodiment of an introducer according to the invention.
Figure 6:
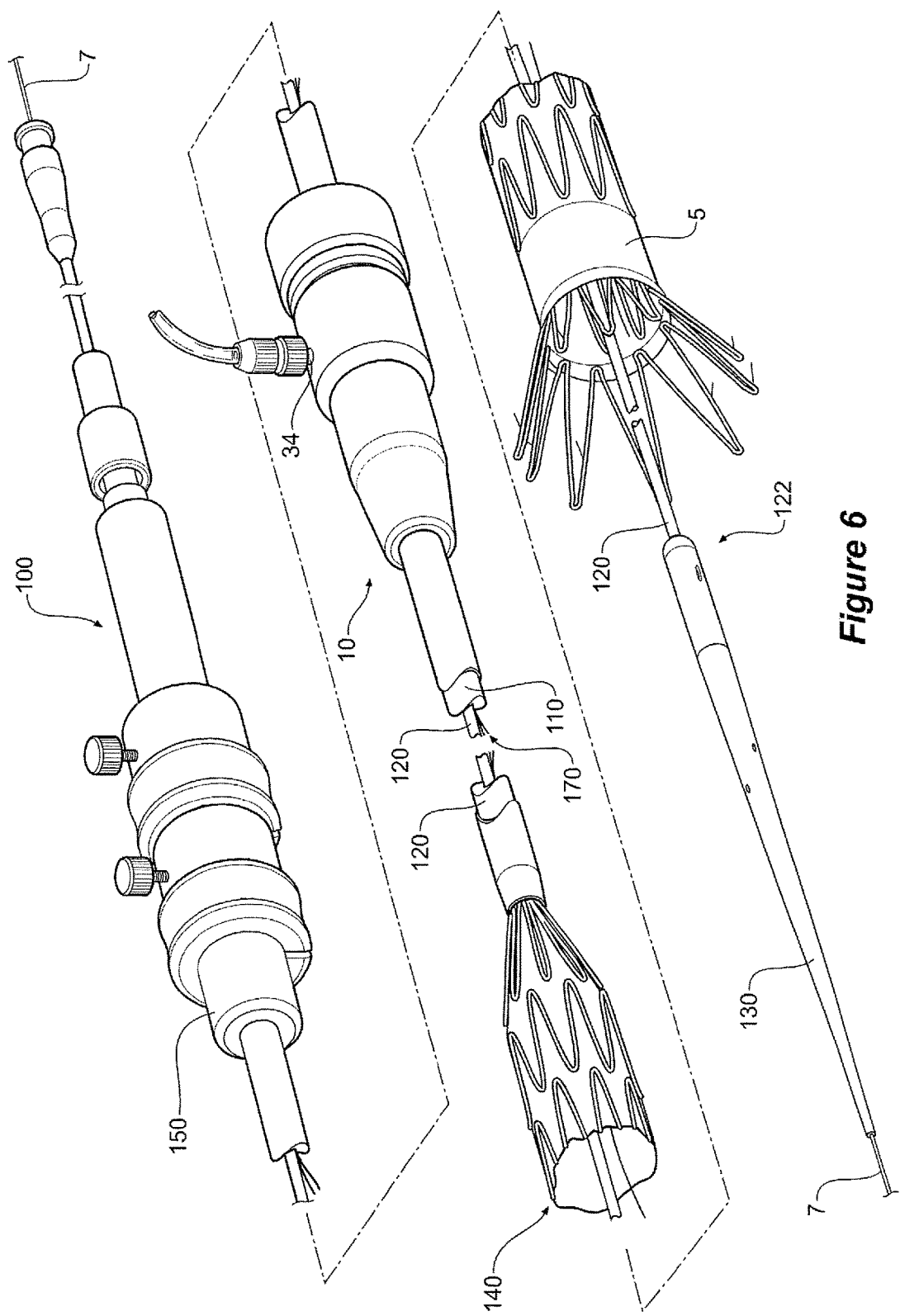
FIG. 6 is an isometric view of an introducer and a delivery assembly according to a third embodiment of the invention.

Referring to FIGS. 1 and 2, an introducer 10 for introduction of a prosthesis, such as the prosthesis 5 shown in FIG. 6, into a lumen of a patient is shown. The introducer 10 comprises a sheath 20, most clearly shown in FIG. 1, having a proximal end 22 and a distal end 28. A housing 30 is mounted to the distal end 28 of the sheath 20. The housing has a passage 35 therethrough as is most clearly shown in FIG. 2. The passage 35 is adapted to receive a delivery assembly, such as the delivery assembly 100 shown in FIG. 6. A port 34 is provided for introducing flushing fluid. The port 34 communicates with the passage 35. The housing 30 shown in FIG. 2 is made from a plurality of parts, including a distal housing portion 38. In other embodiments, more or less component parts may be used to form a suitable housing 30.

A liquid absorbing seal 50 can be seen in FIG. 2. The liquid absorbing seal 50 for sealably receiving a delivery assembly, such as the delivery assembly 100 referred to above. The liquid absorbing seal 50 is disposed within the housing 30 distally of the port 34. In use, introduction of a flushing fluid through the port 34 into the passage 35 results in absorption of a portion of the flushing fluid into the liquid absorbing seal, thereby swelling the liquid absorbing seal.

The liquid absorbing seal 50 comprises a hydrogel. More specifically, the hydrogel comprises a lubricious polymer. A suitable lubricious polymer may include a hydrophilic thermoplastic polyurethane elastomer. The flushing fluid, blood, or other fluids containing water, improve the lubricity of the seal promoting a low coefficient of friction.

In other embodiments, others suitable materials having the liquid-absorbing properties that result in expansion may include, but are not limited to the following: hydrocolloids that are polymer compositions of substantially water-insoluble, slightly cross-linked, partially neutralized polymers prepared from unsaturated polymerizable acid group-containing monomers and cross-linking agents; or any other suitable liquid absorbing materials known in the art.

Figure 3A:
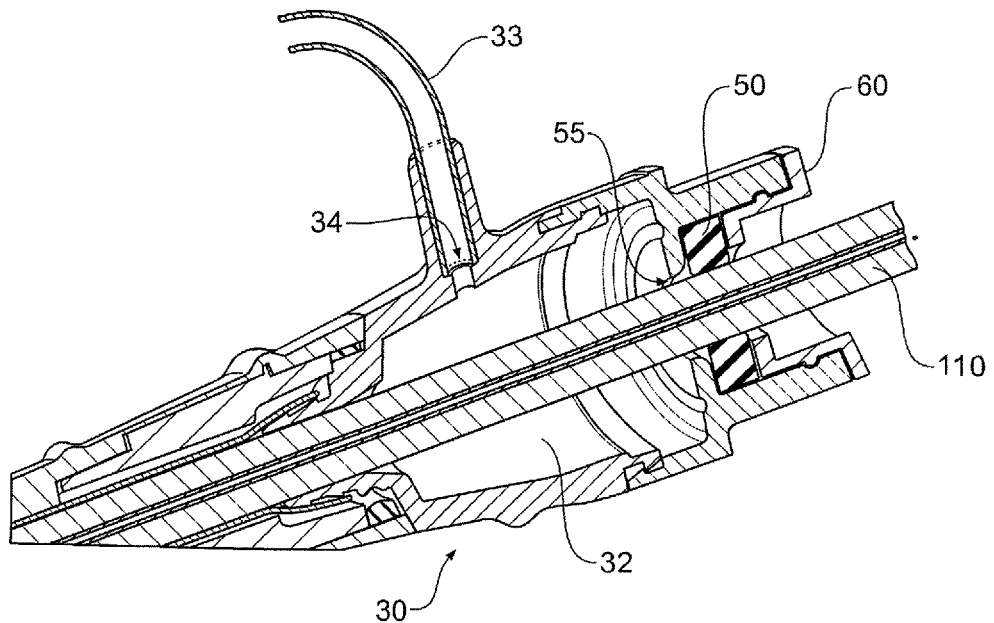
FIGS. 3A and 3B are similar views to that of FIG. 2, but show parts of a delivery assembly inserted through the introducer.
Figure 3B:
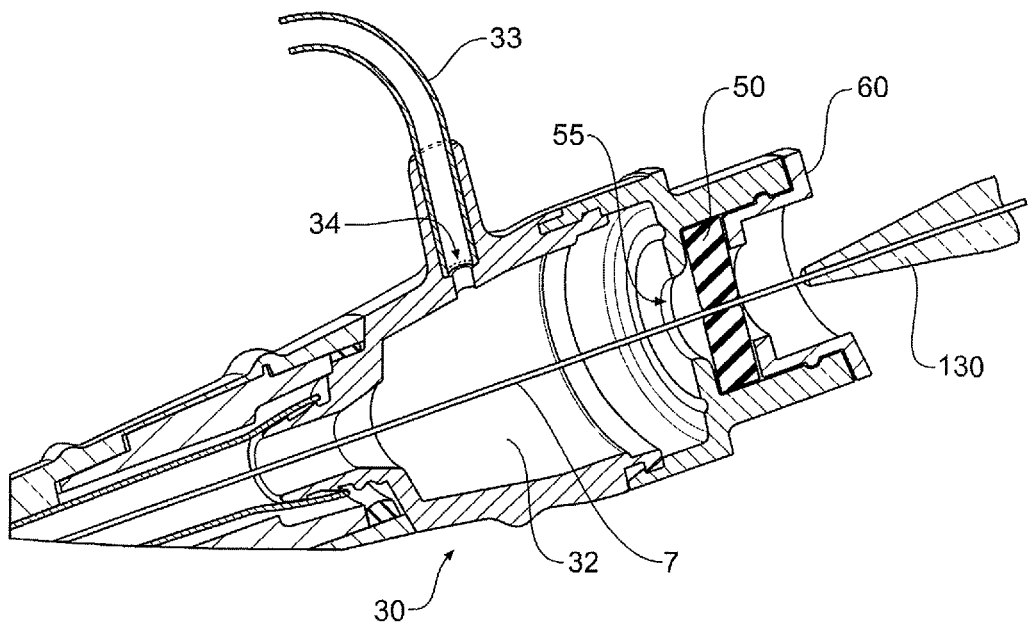

Referring to FIGS. 3A and 3B, it can be seen that the housing 50 includes a fluid receiving chamber hole 55 which has a larger internal diameter than the external diameter of the pusher 110. This allows flushing fluid entering the port 34 via a tube 33 to reach the liquid absorbing seal 50. Once the liquid absorbing seal 50 has absorbed flushing fluid, it expands and becomes more lubricious. This results in the liquid absorbing seal 50 sealing effectively against the outer diameter of the pusher 110, while at the same time allowing relative movement between the pusher 110 and the seal 50.

A cap 60 is provided to retain the liquid absorbing seal 50, as illustrated in FIGS. 3A and 3B. The cap 60 snaps into place within the housing 30. The cap 30 presents a holed disc shaped face to the liquid absorbing seal 50 as can be seen in FIG. 2. Hole 54 through the holed disc shaped face allows access through the seal 50 to the fluid receiving chamber hole 55.

Figure 4:
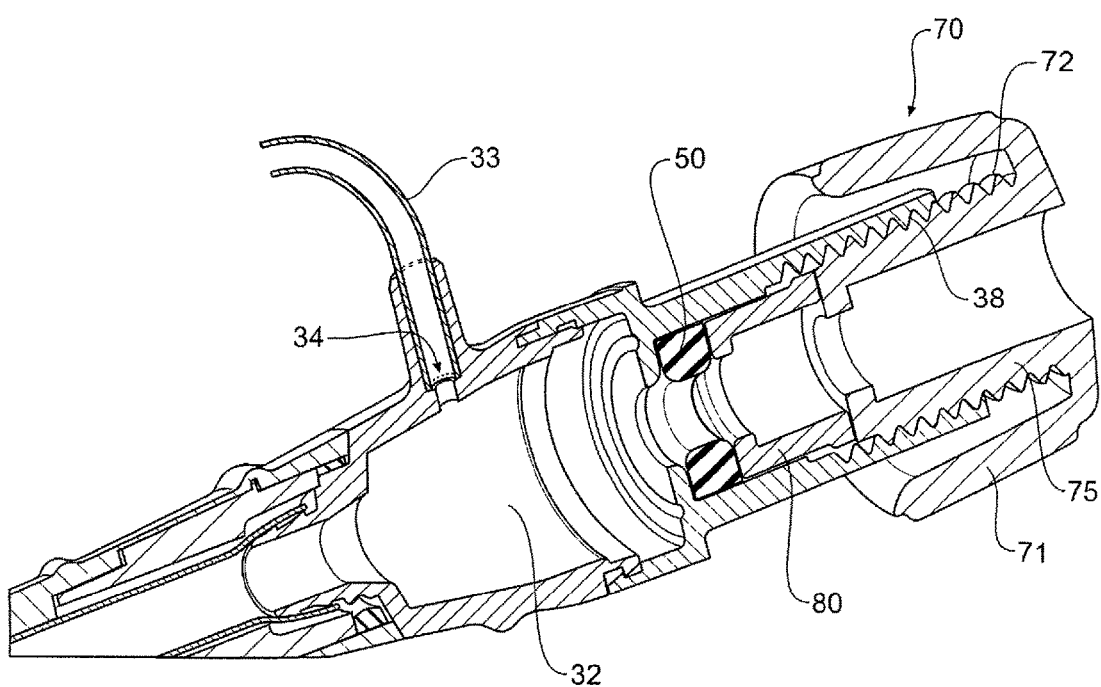
FIG. 4 is a close up cross-sectional view of a second embodiment of an introducer according to the invention.
Figure 5A:
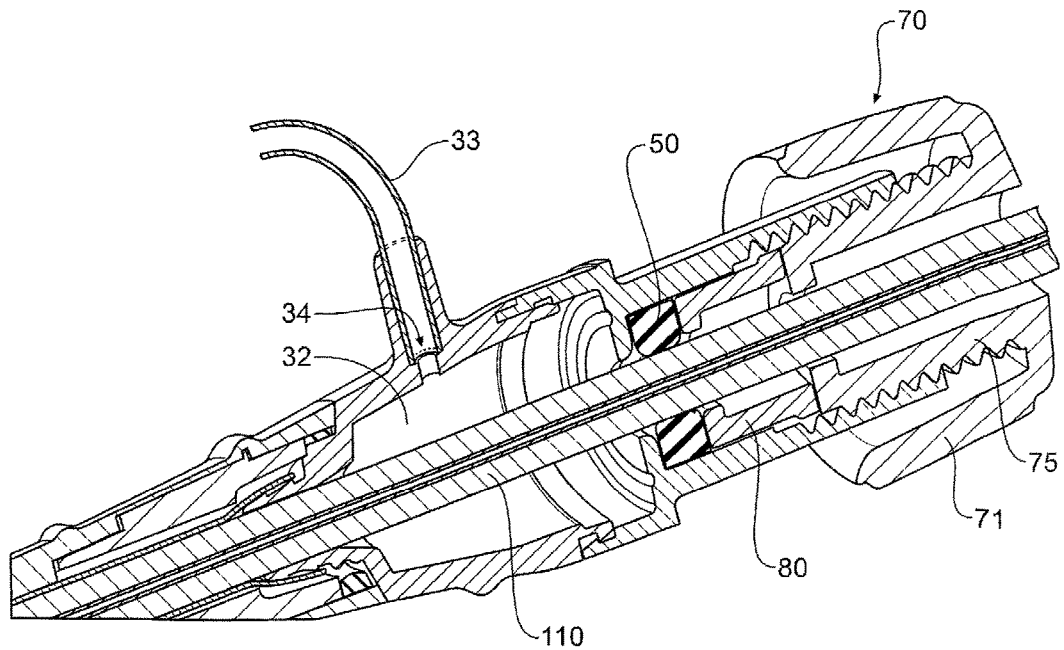
FIGS. 5A and 5B are similar views to that of FIG. 4, but show parts of a delivery assembly inserted through the introducer.
Figure 5B:
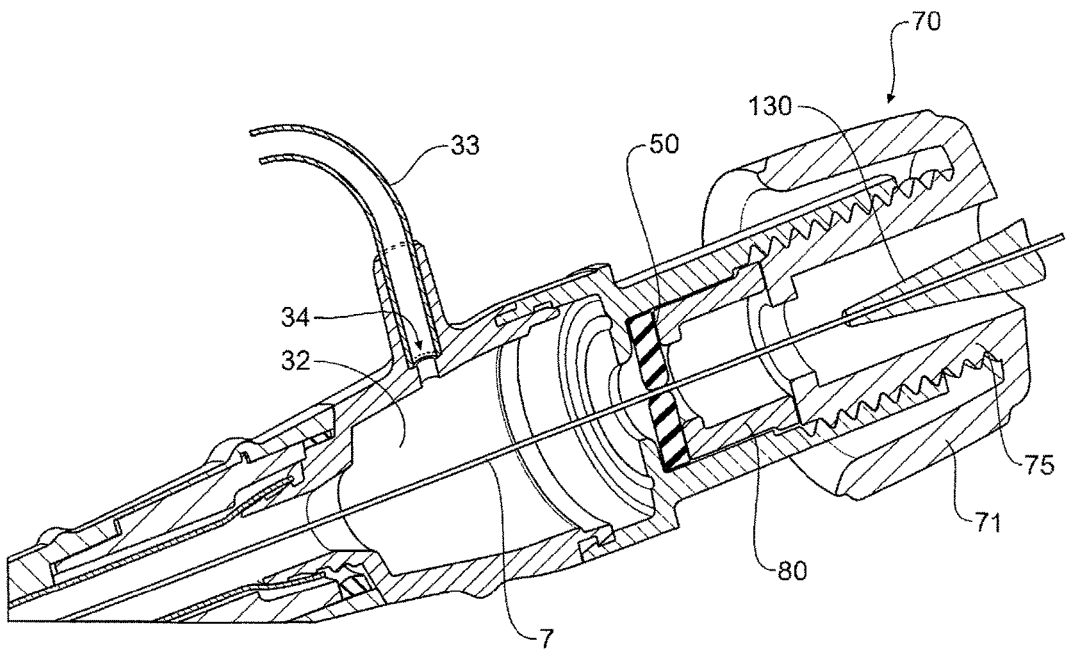

In another embodiment of the invention, illustrated in FIGS. 4, 5A and 5B, an introducer 10 further comprises a compression assembly 70. The compression assembly 70 is operable to compress the liquid absorbing seal 50. The compression assembly 70 comprises an actuator 71 and a compression segment 80. The actuator 71 comprises a rotatable body. The rotatable body is threadably connected to the housing 30. Rotation of the rotatable body pushes the compression segments 80 against the liquid absorbing seal 50 thereby compressing the liquid absorbing seal 50.

The compression segment 80 is a separate component to the rotatable body. The compression segment and the rotatable body are mutually arranged and constructed to allow relative rotation.

With the embodiment of the invention illustrated in FIGS. 4, 5A and 5B, the compression assembly 70 allows in the surgeon or another member of the surgical team to manually adjust the level of compression of the seal 50. For instance, manual adjustment may be desirable when sealing over a fine guide wire such as the guide wire 7 illustrated in FIG. 6. Depending on the characteristics of the seal 50 and on the hydrogel employed, the compression assembly 70 may be of assistance.

Turning now to FIG. 6, an introducer according to either the first embodiment of the invention described above with reference to FIGS. 2, 3A and 3B or with reference to the second embodiment of the invention described above with reference to FIGS. 4, 5A and 5B is shown as part of a delivery assembly according to the invention. The delivery assembly 100 comprises a guide wire catheter 120 having a tip 130 mounted to a proximal end 122 thereof. A distal delivery member 110, which could be referred to as a pusher, is mounted around the guide wire catheter 120 and is located distal of the tip 130. A prosthesis receiving portion 140 is provided between the tip 130 and the distal delivery member 110. The delivery assembly 100 is slidably mounted through the introducer 10. A handle 150 is manipulable to slide the distal delivery member (pusher) 110 through the introducer 10.

An example of the use of embodiments of the invention will now be described.

An introducer 10, together with a delivery assembly 100, as illustrated in FIG. 6 read in conjunction with FIGS. 2, 3A and 3B, is provided packaged and ready for delivery to a hospital.

As a first step, the introducer 10 together with the delivery assembly 100 is unpackaged ready for use. A flushing fluid is then delivered via the tube 33 to the introducer 10. The flushing fluid displaces air within the introducer 10 and the delivery device 100. The flushing fluid is also able to reach the seal 50 through the passage 35, the fluid receiving chamber 32 within the housing 30 and the fluid receiving chamber hole 55. The flushing fluid travels through the fluid receiving chamber hole 55 and wets the seal 50. The flushing fluid also pushes air out of the assembly through to the proximal end 22 of the introducer 10.

At this stage, the seal 50 will tend to absorb some of the flushing fluid and will become more lubricious promoting a lower coefficient of friction.

The introducer 10 can then be introduced to an artery of a patient for instance. For example, the introducer may be inserted through an incision in the femoral artery using the Seldinger method.

Once in position adjacent the target site within the patient (for instance the prosthesis 5 shown in FIG. 6 may be positioned to repair an aneurysmal portion of the aorta), the surgeon may manipulate the handle 150 so as to slide the pusher 110 through the introducer 10.

The liquid absorbing seal 50 described above provides for a very low coefficient of friction between an outer surface of the pusher 110 and an inner surface of the seal 50. This assists the surgeon in fine manipulations and generally facilitates use of the introducer 10 and the delivery assembly 100.

With some procedures, it may be necessary or desirable to leave the introducer 10 in place while extracting the delivery device 100. After the delivery device 100 has been removed, the seal 50 seals against the guide wire 7, as illustrated in FIG. 3B. The ability of the seal 50 to seal against the relatively large diameter pusher 110 and against the relatively small diameter guide wire 7, as is shown respectively in FIGS. 3A and 3B, is important to minimise blood loss.

Blood in contact with the seal 50 contains fluid that is absorbable by the seal 50. This ensures that the seal 50 remains in an expanded and lubricious state during an endovascular procedure.

A further delivery device, or the same delivery device, may be slid along the guide wire 7 so as to enter and pass through the introducer 10. FIG. 3B shows a tip 130 of an introducer just before or after insertion.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. An introducer for introduction of a prosthesis into a lumen of a patient, the introducer comprising: a sheath having a proximal end and a distal end; a housing mounted to the distal end of the sheath, the housing having a passage there-through adapted to receive a delivery assembly; a port for introducing flushing fluid, the port communicating with the passage; a liquid absorbing seal for sealably receiving the delivery assembly, a material of the liquid absorbing seal composed of a hydrogel, the liquid absorbing seal disposed within the housing distally of the port; and a compression assembly operable to compress the liquid absorbing seal comprising a rotatable body and a compression segment, wherein the compression segment is disposed between the liquid absorbing seal and the rotatable body and is a separate component to the rotatable body, and wherein the compression segment and the rotatable body are mutually arranged and constructed to allow rotation of the rotatable body relative to the compression segment; whereby introduction of a flushing fluid through the port into the passage results in absorption of a portion of the flushing fluid into the hydrogel.

2. The introducer of claim 1 wherein the hydrogel comprises a lubricious polymer.

3. The introducer of claim 1 wherein the hydrogel is a hydrophilic thermoplastic polyurethane elastomer.

4. The introducer of claim 1 wherein the rotatable body is threadably connected to the housing, wherein the rotation of the rotatable body pushes the compression segment against the liquid absorbing seal thereby compressing the liquid absorbing seal.

5. The introducer of claim 1, the delivery assembly comprising:
a guide wire catheter;
a tip mounted to a proximal end of the guide wire catheter;
a distal delivery member mounted around the guide wire catheter and located distal of the tip; and
a prosthesis receiving portion between the tip and the distal delivery,
wherein the delivery assembly is slidably mounted through the introducer.

6. The introducer of claim 5 wherein in a first condition the liquid absorbing seal engages an external surface of the distal delivery member, wherein in a second condition the liquid absorbing seal engages an external surface of a guide wire,
whereby in at least the second condition, absorption of fluid swells the liquid absorbing seal.

7. The introducer of claim 5 wherein the hydrogel comprises a lubricious polymer.

8. The introducer of claim 5 wherein the hydrogel is a hydrophilic thermoplastic polyurethane elastomer.

9. The introducer of claim 5 wherein the rotatable body is threadably connected to the housing, wherein the rotation of the rotatable body pushes the compression segment against the liquid absorbing seal thereby compressing the liquid absorbing seal.

10. An introducer and a delivery assembly for introduction of a prosthesis into a lumen of a patient, the introducer comprising: a sheath having a proximal end and a distal end; a housing mounted to the distal end of the sheath, the housing having a passage there-through adapted to receive a delivery assembly; a port for introducing flushing fluid, the port communicating with the passage; a liquid absorbing seal for sealably receiving the delivery assembly, a material of the liquid absorbing seal composed of a hydrophilic thermoplastic polyurethane elastomer hydrogel, the liquid absorbing seal disposed within the housing distally of the port; and a compression assembly operable to compress the liquid absorbing seal comprising a rotatable body and a compression segment, wherein the compression segment is disposed between the liquid absorbing seal and the rotatable body and is a separate component to the rotatable body, and wherein the compression segment and the rotatable body are mutually arranged and constructed to allow rotation of the rotatable body relative to the compression segment, and the delivery assembly comprising: a guide wire catheter; a tip mounted to a proximal end of the guide wire catheter; a distal delivery member mounted around the guide wire catheter and located distal of the tip; and a prosthesis receiving portion between the tip and the distal delivery member wherein the delivery assembly is slidably mounted through the introducer, and wherein in a first condition the liquid absorbing seal engages an external surface of the distal delivery member, and Response to Final Office Action dated Mar. 18, 2019 (BGL No. 12730-1738) wherein in a second condition the liquid absorbing seal engages an external surface of a guide wire, whereby in at least the second condition, absorption of fluid swells the liquid absorbing seal, which is compressed by the compression segment.

* * * * *